(12) United States Patent
Ito et al.

(10) Patent No.: US 12,384,816 B2
(45) Date of Patent: Aug. 12, 2025

(54) BLOOD-BRAIN BARRIER PERMEABLE PEPTIDE

(71) Applicant: NATIONAL UNIVERSITY CORPORATION KUMAMOTO UNIVERSITY, Kumamoto (JP)

(72) Inventors: Shingo Ito, Kumamoto (JP); Sumio Ohtsuki, Kumamoto (JP); Shunsuke Yamaguchi, Kumamoto (JP)

(73) Assignee: NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 40 days.

(21) Appl. No.: 17/260,108

(22) PCT Filed: Jul. 16, 2019

(86) PCT No.: PCT/JP2019/027907
§ 371 (c)(1),
(2) Date: Jan. 13, 2021

(87) PCT Pub. No.: WO2020/017496
PCT Pub. Date: Jan. 23, 2020

(65) Prior Publication Data
US 2022/0009964 A1 Jan. 13, 2022

(30) Foreign Application Priority Data
Jul. 17, 2018 (JP) .................. 2018-134042
Sep. 10, 2018 (JP) .................. 2018-169209

(51) Int. Cl.
| | |
|---|---|
| C07K 7/00 | (2006.01) |
| A61K 9/107 | (2006.01) |
| A61K 9/127 | (2006.01) |
| A61K 9/14 | (2006.01) |
| A61K 9/50 | (2006.01) |
| C07K 7/06 | (2006.01) |
| C07K 7/64 | (2006.01) |
| A61K 38/00 | (2006.01) |

(52) U.S. Cl.
CPC ............... *C07K 7/06* (2013.01); *A61K 9/107* (2013.01); *A61K 9/127* (2013.01); *A61K 9/14* (2013.01); *A61K 9/50* (2013.01); *C07K 7/64* (2013.01); *A61K 38/00* (2013.01)

(58) Field of Classification Search
CPC ...... A61K 9/0085; A61K 47/42; A61K 47/64; A61K 9/107; A61K 9/127; A61K 9/14; A61K 9/50; A61K 38/00; A61K 38/08; C07K 7/06; C07K 7/64; A61P 25/00
See application file for complete search history.

(56) References Cited

U.S. PATENT DOCUMENTS

| | | | |
|---|---|---|---|
| 5,442,043 A | 8/1995 | Fukuta et al. | |
| 9,156,889 B2 | 10/2015 | Nomoto et al. | |
| 9,220,755 B2* | 12/2015 | Chakraborty | .......... A61K 47/54 |
| 2006/0037102 A1* | 2/2006 | Mittendorf | ......... C12N 15/8247 |
| | | | 536/23.6 |
| 2012/0171206 A1* | 7/2012 | Tomlinson | .......... A61K 38/177 |
| | | | 424/134.1 |
| 2019/0054148 A1 | 2/2019 | Ito et al. | |

FOREIGN PATENT DOCUMENTS

| | | |
|---|---|---|
| JP | 06-228199 | 8/1994 |
| WO | 2012105595 | 8/2012 |
| WO | 2016148213 | 9/2016 |
| WO | 2016186140 | 11/2016 |

OTHER PUBLICATIONS

UniProtKB/Swiss-Prot. Accession No. P29788 (Oct. 2, 2024, entry version 211). (Year: 2024).*
Coloma MJ et al., "Transport Across the Primate Blood-Brain Barrier of a Genetically Engineered Chimeric Monoclonal Antibody to the Human Insulin Receptor," Pharmaceutical Research, vol. 17, (Nov. 3, 2000).
Abulrob A et al., "The blood-brain barrier transmigrating single domain antibody: mechanisms of transport and antigenic epitopes in human brain endothelial cells," Journal of Neurochemistry, 95, 1201-1214 (2005).
Schwarse S R et al., "In Vivo Protein Transduction: Delivery of a Biologically Active Protein into the Mouse" Science, 285. 1569 (Sep. 3, 1999).
Fu A. et al., "Targeted Delivery of Proteins into the Central Nervous System Mediated by Rabies Virus Glycoprotein-Derived Peptide," Pharm Res 29, 1562-1569 (2012).
Demeula M et al., "Identification and Design of Peptides as a New DrugDelivery System for the Brain," Journal of Pharmacology and Experimental Therapeutics, 324, (3), 1064-1072 (Mar. 2008).
Kumar P et al., "Transvascular delivery of small interfering RNA to the central nervous system," Nature, 448(7149) 39-43 (2007).
International Search Report and Written Opinion for PCT/JP2019/027807 mailed on Sep. 3, 2019.
Yamaguchi, S. "Identification of cyclic peptides for facilitation of transcellular transport of phages across intestinal epithelium in vitro and in vivo", Journal of Controlled Release, 2017, vol. 262, pp. 232-238.

* cited by examiner

*Primary Examiner* — Jeanette M Lieb
(74) *Attorney, Agent, or Firm* — HUNTON ANDREWS KURTH LLP

(57) ABSTRACT

The present invention has an object of providing a novel peptide that is permeable to the blood-brain barrier. The present invention provides a blood-brain barrier permeable peptide containing an amino acid sequence: SLSHSPQ (SEQ ID NO: 1) (where P may be substituted). The present invention also provides a carrier molecule for intracerebral delivery containing the peptide, a complex composed of the peptide and a target molecule that is allowed to permeate the blood-brain barrier, and a blood-brain barrier permeable composition containing the complex.

16 Claims, 6 Drawing Sheets

Specification includes a Sequence Listing.

SEQUENCE LISTING

```
<160> NUMBER OF SEQ ID NOS: 8

<210> SEQ ID NO 1
<211> LENGTH: 7
<212> TYPE: PRT
<213> ORGANISM: Artificial Sequence
<220> FEATURE:
<223> OTHER INFORMATION: Synthesized Peptide

<400> SEQUENCE: 1

Ser Leu Ser His Ser Pro Gln
1               5

<210> SEQ ID NO 2
<211> LENGTH: 9
<212> TYPE: PRT
<213> ORGANISM: Artificial Sequence
<220> FEATURE:
<223> OTHER INFORMATION: Synthesized peptide
<220> FEATURE:
<221> NAME/KEY: DISULFID
<222> LOCATION: (1)..(9)

<400> SEQUENCE: 2

Cys Ser Leu Ser His Ser Pro Gln Cys
1               5

<210> SEQ ID NO 3
<211> LENGTH: 13
<212> TYPE: PRT
<213> ORGANISM: Artificial Sequence
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa at position 1 represents any amino acid.
      Xaa could be 1, 2, 3, 4, 5, 6, 7, 8, 9 and/or 10 amino acids
<220> FEATURE:
<221> NAME/KEY: DISULFID
<222> LOCATION: (2)..(12)
<220> FEATURE:
<221> NAME/KEY: misc_feature
<222> LOCATION: (3)..(3)
<223> OTHER INFORMATION: Xaa at position 3 represents any amino acid.
      XXa could be 1, 2, 3, 4 and/or 5 amino acids
<220> FEATURE:
<221> NAME/KEY: misc_feature
<222> LOCATION: (11)..(11)
<223> OTHER INFORMATION: Xaa at position 11 represents any amino acid.
      Xaa could be 1, 2, 3, 4 and/or 5 amino acids
<220> FEATURE:
<221> NAME/KEY: misc_feature
<222> LOCATION: (13)..(13)
<223> OTHER INFORMATION: Xaa at position 13 represents any amino acid.
      Xaa could be 1, 2, 3, 4, 5, 6, 7, 8, 9 and/or 10 amino acids

<400> SEQUENCE: 3

Xaa Cys Xaa Ser Leu Ser His Ser Pro Gln Xaa Cys Xaa
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Synthesized Peptide

<400> SEQUENCE: 4

Gln Pro Ser His Ser Leu Ser
1               5
```

```
<210> SEQ ID NO 5
<211> LENGTH: 14
<212> TYPE: PRT
<213> ORGANISM: Artificial Sequence
<220> FEATURE:
<223> OTHER INFORMATION: Synthesized Peptide

<400> SEQUENCE: 5

Ala Cys Ser Leu Ser His Ser Pro Gln Cys Gly Gly Gly Ser
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthesized peptide

<400> SEQUENCE: 6

Cys Ser Leu Ser His Ser Pro Gln Cys
1               5

<210> SEQ ID NO 7
<211> LENGTH: 9
<212> TYPE: PRT
<213> ORGANISM: Artificial Sequence
<220> FEATURE:
<223> OTHER INFORMATION: Synthesized peptide

<400> SEQUENCE: 7

Ala Cys Ser Leu Ser His Ser Pro Gln
1               5

<210> SEQ ID NO 8
<211> LENGTH: 14
<212> TYPE: PRT
<213> ORGANISM: Artificial Sequence
<220> FEATURE:
<223> OTHER INFORMATION: Synthesized Peptide
<220> FEATURE:
<221> NAME/KEY: DISULFID
<222> LOCATION: (2)..(10)
<220> FEATURE:
<221> NAME/KEY: misc_feature
<222> LOCATION: (3)..(3)
<223> OTHER INFORMATION: Xaa at position 3 represents any amino acid.
<220> FEATURE:
<221> NAME/KEY: misc_feature
<222> LOCATION: (4)..(4)
<223> OTHER INFORMATION: Xaa at position 4 represents any amino acid.
<220> FEATURE:
<221> NAME/KEY: misc_feature
<222> LOCATION: (5)..(5)
<223> OTHER INFORMATION: Xaa at position 5 represents any amino acid.
<220> FEATURE:
<221> NAME/KEY: misc_feature
<222> LOCATION: (6)..(6)
<223> OTHER INFORMATION: Xaa at position 6 represents any amino acid.
<220> FEATURE:
<221> NAME/KEY: misc_feature
<222> LOCATION: (7)..(7)
<223> OTHER INFORMATION: Xaa at position 7 represents any amino acid.
<220> FEATURE:
<221> NAME/KEY: misc_feature
<222> LOCATION: (8)..(8)
<223> OTHER INFORMATION: Xaa at position 8 represents any amino acid.
<220> FEATURE:
<221> NAME/KEY: misc_feature
<222> LOCATION: (9)..(9)
<223> OTHER INFORMATION: Xaa at position 9 represents any amino acid.
```

```
<400> SEQUENCE: 8

Ala Cys Xaa Xaa Xaa Xaa Xaa Xaa Xaa Cys Gly Gly Gly Ser
1               5                   10
```

BLOOD-BRAIN BARRIER PERMEABLE PEPTIDE

CROSS-REFERENCE TO RELATED APPLICATION(S)

This application relates to, and claims the benefit and priority from International Patent Application No. PCT/JP2019/027907 filed on Jul. 16, 2019, and published as International Publication WO 2020/017496 on Jan. 23, 2020, which claims the benefit and priority from Japanese Patent Application No. 2018-134042 filed on Jul. 17, 2018 and Japanese Patent Application No. 2018-169209 filed on Sep. 10, 2018.

SEQUENCE LISTING

The instant application contains a Sequence Listing which has been submitted via EFS-Web and is hereby incorporated by reference in its entirety. The ASCII text tile, created on Mar. 26, 2025, is named 17031US10v2_ST25.txt, and is 3,457 bytes in size.

TECHNICAL FIELD

The present invention relates to a peptide that is permeable to the blood-brain barrier (BBB). The present invention also relates to an intracerebral delivery carrier molecule or complex containing the peptide, and further to a pharmaceutical composition containing the peptide.

BACKGROUND ART

In order to maximize the effect of a drug for treating central nervous system diseases, it is necessary to efficiently deliver the drug to the brain. However, it is known that water-soluble drugs and proteins administered or diffused in blood hardly transfer into the brain. This is because BBB acts as a physical and dynamic barrier that separates blood from brain tissue fluid, strictly limiting the passive diffusion of substances into the brain. Hence, in order to deliver a target substance administered in blood into the brain, it is essential to develop a carrier molecule that efficiently permeates the BBB.

Carrier molecules for intracerebrally-delivering substances that do not transfer into the brain, such as water-soluble drugs and proteins, have been reported. So far, to improve the BBB permeability of medicinal products for intracerebral delivery of drugs via the BBB, drug delivery systems (DDS) using BBB permeable carriers such as monoclonal antibodies against the transferrin receptors expressed on the BBB (J-Brain Cargo (registered trademark) manufactured by JCR Co., Ltd.), monoclonal antibodies against the insulin receptors, and BBB permeable antibodies: FC5; certain cell membrane permeable peptides: Tat and RVG-9R peptide, RDP peptide or Angiopep, have been developed (Non-Patent Documents 1 to 6). However, many DDSs using existing BBB permeable carriers have a problem that the size of substance to be permeated is limited. Another problem is that DDSs using antibodies have immunogenicity.

CITATION LIST

Non-Patent Document

Non-Patent Document 1: Coloma M J, et al., Pharm Res. 2000 (3): 266-74

Non-Patent Document 2: Abulrob A., et al., J Neurochem. 2005 95 (4): 1201-14

Non-Patent Document 3: Schwarze S. R., et al., Science, 1999, 285, 1569-1572

Non-Patent Document 4: Fu A., et al., Pharm. Res, 2012, 29, 1562-1569

Non-Patent Document 5: Demeula M., et al., J Pharmacol Exp Ther. 2008; 324 (3): 1064-72

Non-Patent Document 6: Kumar P., et al., Nature, 2007 448 (7149): 39-43

SUMMARY OF THE INVENTION

Technical Problem

It is an object of the present invention to provide a novel peptide that is permeable to the blood-brain barrier (BBB).

Solution to Problem

The present inventors have intensively studied to solve the problems and resultantly found that a relatively short peptide containing a specific amino acid sequence is permeable to the BBB, leading to completion of the present invention.

The present invention includes the followings.

[1] A blood-brain barrier permeable peptide comprising any of the following amino acid sequences:
  (i) a sequence consisting of SLSHSPQ (SEQ ID NO: 1), or
  (ii) an amino acid sequence shown in SEQ ID NO: 1, in which P is substituted with an amino acid selected from the group consisting of A, I, L, V, M, F. W, Y, S, T, N, Q, H and G (preferably the group consisting of A, I, L, V, M, S, T, N, Q and G, and more preferably the group consisting of A, I, L, V, S, T and G.).

[2] The blood-brain barrier permeable peptide according to the above [1], which comprises at least one unnatural amino acid.

[3] The blood-brain barrier permeable peptide according to the above [1] or [2], wherein the peptide is a cyclic peptide.

[4] The blood-brain barrier permeable peptide according to the above [1], wherein the peptide is any one of the followings (a) to (f):
  (a) a peptide consisting of an amino acid sequence: SLSHSPQ (SEQ ID NO: 1),
  (b) a peptide having 1 to 5 amino acids at the C-terminal and/or the N-terminal of the amino acid sequence of SLSHSPQ (SEQ ID NO: 1),
  (c) a peptide consisting of an amino acid sequence: CSLSHSPQC (SEQ ID NO: 2) in which cysteine residues in the sequence are disulfide-bonded.
  (d) a peptide having 1 to 10 amino acids at the C-terminal and/or N-terminal of the amino acid sequence of CSLSHSPQC (SEQ ID NO: 2), in which cysteine residues in the sequence are disulfide-bonded,
  (e) a peptide represented by an amino acid sequence of the following formula (1) (SEQ ID NO: 3):

[Chemical Formula 1]

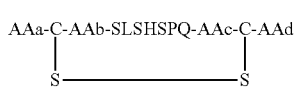

(wherein, AAa and AAd each independently represent 1 to 10 amino acids, and AAb and AAc each independently represent 1 to 5 amino acids), or (f) a peptide having 1 to 15 arbitrary amino acids at the C-terminal and N-terminal of the amino acid sequence of SLSHSPQ (SEQ ID NO: 1), in which any of the amino acids existing at both ends of the sequence are crosslinked together, (g) the peptide as described in any one of (a) to (f) above, in which P in the amino acid sequence SLSHSPQ (SEQ ID NO: 1) is substituted with an amino acid selected from the group consisting of A, I, L, V, M, F, W, Y, S, T, N, Q, H and G (preferably the group consisting of A, I, L, V, M, S, T, N, Q and G, and more preferably the group consisting of A, I, L, V, S, T and G.).

[5] The blood-brain barrier permeable peptide according to the above [4], which comprises at least one unnatural amino acid.

[6] A carrier for intracerebral delivery comprising the peptide as described in any one of the above [1] to [5].

[7] The carrier for intracerebral delivery according to the above [6], wherein the carrier for intracerebral delivery comprises the peptide as described in any one of the above [1] to [5], and a carrier molecule for drug delivery selected from the group consisting of liposomes, nanocarriers, exosomes, phages, polyrotaxanes, cyclodextrins, microcapsules and micelles.

[8] The carrier for intracerebral delivery according to the above [6] or [7], wherein the carrier is used with a substance selected from the group consisting of transferrin, fibrinogen, and a peptide containing RGD0 sequence.

[9] The carrier for intracerebral delivery according to the above [6] or [7], further comprising a substance selected from the group consisting of transferrin, fibrinogen, and a peptide containing RGD sequence.

[10] A composition comprising the carrier for intracerebral delivery as described in any one of the above [6] to [9] and a drug to be delivered into the brain.

[11] The composition according to the above [10], wherein the drug is a molecule that exhibits a pharmacological action in the brain or an intracerebral imaging molecule.

[12] The composition according to the above [11], wherein the molecule that exhibits a pharmacological action in the brain is a small molecular compound, a polypeptide, an oligopeptide, a protein or a nucleic acid.

[13] A pharmaceutical composition for preventing and/or treating a brain disease, which comprises the composition as described in any one of the above to and a pharmacologically acceptable additive.

[14] A complex comprising the peptide as described in any one of the above [1] to [5] and a molecule that permeates the blood-brain barrier with the peptide.

[15] The complex according to the above [14], wherein the complex is used with a substance selected from the group consisting of transferrin, fibrinogen, and a peptide containing RGD sequence.

[16] The complex according to the above [14], further comprising a substance selected from the group consisting of transferrin, fibrinogen, and a peptide containing RGD sequence.

[17] The complex according to any one of the above to [16], wherein the molecule is a molecule that exhibits a pharmacological action in the brain or an intracerebral imaging molecule.

[18] The complex according to any one of the above to [16], wherein the molecule is a small molecular compound, a polypeptide, an oligopeptide, a protein or a nucleic acid.

[19] A pharmaceutical composition for preventing and/or treating a brain disease, which comprises the complex as described in any one of the above to and a pharmacologically acceptable additive.

[20] A composition comprising a mixture of the peptide as described in any one of the above [1] to [5] with at least one molecule that permeates the blood-brain barrier in the presence of the peptide, and a pharmacologically acceptable additive.

[21] The composition according to the above [20], wherein the mixture further comprises a substance selected from the group consisting of transferrin, fibrinogen, and a peptide containing the RGD sequence.

[22] The composition according to the above or [21], wherein the molecule is one or more molecules selected from the group consisting of small molecular compounds, polypeptides, oligopeptides, proteins, nucleic acids, liposomes, nanocarriers, exosomes, phages, polyrotaxanes and intracerebral imaging molecules.

[23] A pharmaceutical composition for preventing and/or treating a brain disease, which comprises the composition as described in any one of the above to [22].

[24] A method for preventing and/or treating a brain disease, comprising administering a prophylactically and/or therapeutically effective amount of the pharmaceutical composition as described in the above [13], or to a subject in need of prevention and/or treatment of the brain disease.

Advantageous Effect of the Invention

According to the present invention, a novel blood-brain barrier (BBB) permeable peptide that permeates the BBB is provided.

DESCRIPTION OF EMBODIMENTS

Figure 1:
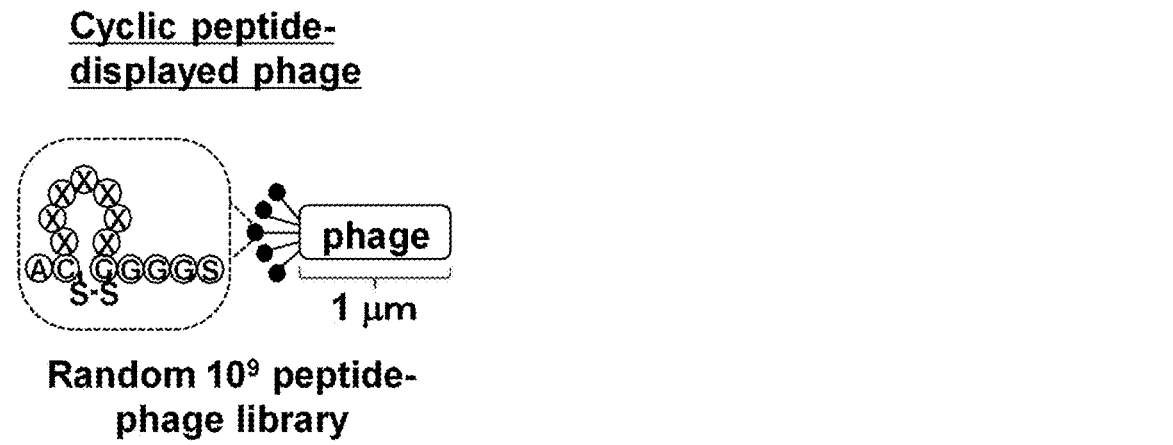
FIG. 1 is a view showing a phage and a cyclic amino acid structure (SEQ ID NO: 8) displayed on the phage.

Hereinafter, the present invention will be illustrated with reference to the exemplary embodiments along with preferred methods and materials which can be used in practice of the present invention. Unless otherwise specified in the sentences, any technical terms and scientific terms used in the present specification have the same meaning as those generally understood by those of ordinary skill in the art to which the present invention belongs. Any materials and methods equivalent or similar to those described in the present specification can be used for practicing the present invention. All publications and patents cited herein in connection with the present invention described herein are incorporated by reference, for example, as indicating methodology, materials, etc. that can be used in the present invention.

In the present specification, when the expression "X to Y" is used, the expression is used to mean that X is included as the lower limit and Y is included as the upper limit, or that X is includes as the upper limit and Y is included as the lower limit.

When amino acids are indicated in the present specification, they are represented by one letter notation: A (alanine), R (arginine), N (asparagine), D (aspartic acid), C (cysteine), Q (glutamine), E (glutamic acid), G (glycine), H (histidine), I (isoleucine), L (leucine), K (lysine), M (methionine), F (phenylalanine), P (proline), S (serine), T (threonine), W (tryptophane), Y (tyrosine) or V (valine).

(1) BBB Permeable Peptide

The BBB permeable peptide of the present invention (hereinafter, may be simply referred to as the peptide of the present invention) is characterized by having an amino acid sequence: SLSHSPQ (SEQ ID NO: 1) or a similar sequence thereof. The similar sequence means a sequence SLSHSPQ shown in SEQ ID NO: 1 in which P is substituted with an amino acid selected from the group consisting of A, I, L, V, M, F, W, Y, S, T, N, Q, H and G, preferably with an amino acid selected from the group consisting of A, I, L, V, M, S, T, N, Q and G, and more preferably with an amino acid selected from the group consisting of A, I, L, V, S, T and G, and in the present specification, it may be simply referred to as a similar sequence of SEQ ID NO: 1. The peptide of the present invention is not limited to those composed entirely of natural L-form amino acids, and may be composed of either L-form or D-form amino acids, and may be composed of a mixture of L-form and D-form amino acids. In the peptide of the present invention, unnatural amino acids such as derivatives having a partially modified structure of natural amino acids can also be used, in addition to amino acids having an L-form configuration which are naturally occurring amino acids. The unnatural amino acid is not particularly limited, and any known amino acid can be used. For example, amino acids having a D-form configuration and N-methyl amino acids can be effectively used for the peptides of the present invention because they are not easily decomposed by proteolytic enzymes. Therefore, it is preferable that at least a part of the amino acid sequence of the peptide of the present invention is composed of non-natural amino acids such as D-form amino acids or N-methyl amino acids.

The BBB permeable peptide of the present invention is characterized by having an amino acid sequence: SLSHSPQ (SEQ ID NO: 1) or a similar sequence of SEQ ID NO: 1, and is meant to include a reverse-chain peptide of the sequence. For example, when a peptide containing the amino acid sequence SLSHSPQ (SEQ ID NO: 1) is mentioned, it means to include either a peptide containing the sequence in the order of (N-terminal)-SLSHSPQ (SEQ ID NO: 1)-(C-terminal) or a peptide containing the sequence in the order of (N-terminal)-QPSHSLS-(C-terminal) (SEQ ID NO: 4). The same applies also to an amino acid sequence: CSLSHSPQC (SEQ ID NO: 2) and other sequences.

The BBB permeable peptide of the present invention is a peptide containing an amino acid sequence: SLSHSPQ (SEQ ID NO: 1) or a similar sequence of SEQ ID NO: 1, and includes, but not limited to, for example, peptides shown in any one of (a) to (f) below.

(a) a peptide consisting of the amino acid sequence: SLSHSPQ (SEQ ID NO: 1), (b) a peptide having 1 to 5 arbitrary amino acids at the C-terminal and/or N-terminal of the amino acid sequence of SLSHSPQ (SEQ ID NO: 1),
(c) a peptide consisting of the amino acid sequence: CSLSHSPQC (SEQ ID NO: 2) in which cysteine residues in the sequence are disulfide-bonded,
(d) a peptide having 1 to 10 arbitrary amino acids at the C-terminal and/or N-terminal of the amino acid sequence of CSLSHSPQC (SEQ ID NO: 2), in which cysteine residues in the sequence are disulfide-bonded,
(e) a peptide represented by an amino acid sequence of the following formula (1) (SEQ ID NO: 3):

[Chemical Formula 2]

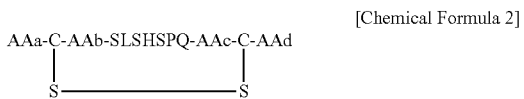

(wherein, AAa and AAd each independently represent 1 to 10 arbitrary amino acids, and AAb and AAc each independently represent 1 to 5 arbitrary amino acids), or
(f) a peptide having 1 to 15 arbitrary amino acids at the C-terminal and N-terminal of the amino acid sequence of SLSHSPQ (SEQ ID NO: 1), in which arbitrary amino acids existing at both ends of the sequence are crosslinked.
(g) the peptide as described in any one of (a) to (f) above, in which P in the amino acid sequence SLSHSPQ (SEQ ID NO: 1) is substituted with an amino acid selected from the group consisting of A, I, L, V, M, F, W, Y, S, T, N, Q, H and G, preferably with an amino acid selected from the group consisting of A, I, L, V, M, S, T, N, Q and G, and more preferably with an amino acid selected from the group consisting of A, I, L, V, S, T and G.

The peptide of the present invention represented by (b) above is a peptide having 1 to 5, preferably 1 to 3, and further preferably 1 to 2 arbitrary amino acids at the C-terminal and/or N-terminal of the amino acid sequence of SEQ ID NO: 1, respectively. The type of the amino acid(s) added to the C-terminal or N-terminal is not particularly limited, and any amino acid(s) is added. Each of the amino acids to be added may be either a natural amino acid or an unnatural amino acid, or any modified amino acid thereof.

The peptide of the present invention represented by (d) above is a cyclic peptide containing the amino acid sequence of SEQ ID NO: 1 in the ring and in which the cysteine residues at both ends of the sequence form a disulfide bond, wherein the peptide further has 1 to 10, preferably 1 to 7, and more preferably 1 to 5 arbitrary amino acids at the cysteine residue(s) at the C-terminal and/or N-terminal. The type of the amino acid(s) to be added to the cysteine at the C-terminal or N-terminal is not particularly limited, and any amino acid(s) is added. Each of the amino acids to be added may be either a natural amino acid or an unnatural amino acid, or any modified amino acid thereof.

The peptide of the present invention represented by (e) above is a cyclic peptide represented by the following formula (SEQ ID NO: 3).

[Chemical 3]

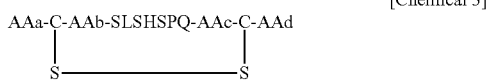

Here, AAa and AAd each independently represent 1 to 10, preferably 1 to 7, and more preferably 1 to 5 arbitrary amino acids, and AAb and AAc independently represent 1 to 5, preferably 1 to 3, and more preferably 1 to 2 arbitrary amino acids. In the formula, each amino acid represented by AAa to AAd may be either a natural amino acid or an unnatural amino acid, or any modified amino acid thereof.

The peptide of the present invention represented by (f) above is a peptide having 1 to 15, preferably 3 to 15, further preferably 5 to 15, and more further preferably 5 to 10 arbitrary amino acids at the C-terminal and N-terminal of the amino acid sequence of SLSHSPQ (SEQ ID NO: 1) in which arbitrary amino acids existing at both ends of the sequence are crosslinked, that is, it is a cyclic peptide having the amino acid sequence of SEQ ID NO: 1 in the ring. The type of the amino acid to be added to the C-terminal or N-terminal is not particularly limited, and any amino acid is added. Each of the amino acids to be added may be either a natural amino acid or an unnatural amino acid, or any modified amino acid thereof. Further, the positions of the amino acids forming the crosslink are not limited, and any of the cases where the positions are at both terminals of the full-length peptide, one position is at the terminal of the full-length peptide, and any positions are not at the terminal of the full-length peptide may be permissible.

For cyclization of forming a crosslink, a known technique used in the field of amino acid synthesis technique can be used without limitation. Examples of typical cyclization modes include a disulfide bond (SS bond), an amide bond, a thioether bond, an olefin bond, and a crosslink via a lactam ring. In the case of a disulfide bond (SS bond), the above embodiments (c) to (d) are included. Specific examples thereof include, but not limited to, cyclization of two penicillamine residues by connecting them with a disulfide bridge (Mosberg et al., P.N.A.S. US, 80:5871, 1983), cyclization made by forming an amide bond between lysine and aspartic acid (Flora et al., Bioorg. Med. Chem. Lett. 15 (2005) 1065-1068), or cyclization made by a condensation reaction following introducing an amino acid derivative containing a crosslinked portion, into which a thioether bond has been introduced previously, into a peptide bond (Melin et al., U.S. Pat. No. 6,143,722), and cyclization made by crosslinking(S)-α-(2'-pentenyl) alanines introduced into the main chain using an olefin metathesis reaction (Schafmeister et al., J. Am. Chem. Soc., 122, 5891-5892, 2000). Further, any spacer can also be introduced between amino acids constituting the crosslink. Examples of the spacer include, but not limited to, polyethylene glycol of any length. Additionally, techniques have been reported in which an amino acid having a special structure for forming a crosslink, other than the above amino acids, is introduced at the position of an amino acid constituting an anchor portion, to form a crosslink, and these can also be used in synthesis of the peptide of the invention.

The peptide of the present invention represented by (g) above is any one of the peptides represented by (a) to (f) above in which P in the sequence SLSHSPQ shown in SEQ ID NO: 1 is substituted with an amino acid selected from the group consisting of A, I, L, V, M, F, W, Y, S. T, N, Q, H and G, preferably with an amino acid selected from the group consisting of A, I, L, V, M, S, T, N, Q and G, and more preferably with an amino acid selected from the group consisting of A, I, L, V, S, T and G.

A BBB permeable peptide of the present invention is characterized by having an amino acid sequence: SLSHSPQ (SEQ ID NO: 1) or a similar sequence of SEQ ID NO: 1, and may be linear or cyclic, and it is preferably a cyclic peptide having the above sequence in the ring The term "cyclic peptide" used in the present specification means to include any of the cases in which the N-terminal and C-terminal of the peptide are linked to form a ring, one of the N-terminal or C-terminal of the peptide and the amino acid residue at any place in the peptide chain are connected to form a cycle, or amino acid residues at any two positions of the peptide chain are connected to form a ring. The connecting mode to form a ring includes any of the cases in which amino acid residues are bonded to each other directly, or a linker constituting the crosslink is included therebetween.

As a method of forming a cyclic peptide, various methods have been reported, and a BBB permeating peptide of the present invention having a cycle can be produced by appropriately using these methods. These reports include a method of directly connecting amino acid residues including a modified amino acid, and a method of crosslinking two amino acid residues via a linker. The type of a ring and the mode of ring formation when forming a ring in the peptide of the present invention are not particularly limited, and any types and modes can be selected depending on an intended purpose. For example, in a certain embodiment, a disulfide bond between cysteine residues is convenient and preferred, while in other embodiments, cyclization by another connecting mode, e.g., an olefin bond, can also be selected, if resistance to degradation in blood is desired.

When amino acid residues at both terminals of a peptide form a crosslink or when any amino acid residues at any position of a peptide chain, preferably the position located at both sides of the amino acid sequence of SEQ ID NO: 1 (including the position adjacent to the sequence and at the position where one or several amino acid residues are present between the sequence) form a crosslink in the peptide of the present invention, the crosslinking means includes, but not limited to, a crosslink via, for example, a disulfide bond (SS bond), an amide bond, a thioether bond or an olefin bond. Examples thereof include, but not limited to, cyclization of two penicillamine residues by connecting them with a disulfide bridge (Mosberg et al., P.N.A.S. US, 80:5871, 1983), cyclization made by forming an amide bond between lysine and aspartic acid (Flora et al., Bioorg. Med. Chem. Lett. 15 (2005) 1065-1068), or cyclization made by a condensation reaction following introducing an amino acid derivative containing a crosslinked portion, into which a thioether bond has been introduced previously, into a peptide bond (Melin et al., U.S. Pat. No. 6,143,722), and cyclization made by crosslinking(S)-α-(2'-pentenyl) alanines introduced into the peptide chain using an olefin metathesis reaction (Schafmeister et al., J. Am. Chem. Soc., 122, 5891-5892, 2000). Additionally, a crosslink disclosed in WO2012/121057 having a special structure in the amino acid residue portion functioning as an anchor for the crosslink can also be used.

The peptide of the present invention, which is a cyclic peptide, includes, but not limited to, for example, the following peptides.

The peptide of the present invention represented by (a) above has the amino acid sequence shown in SEQ ID NO: 1, and its C-terminal and N-terminal may be bonded directly or via any spacer, to form a ring.

In the peptide of the present invention represented by (b) above, its C-terminal and N-terminal may be bonded directly or via any spacer, to form a ring, alternatively, amino acid residues at arbitrary positions of the peptide chain may be crosslinked, preferably to include the amino acid sequence of SEQ ID NO: 1 in the ring, to form a ring.

In the peptides of the present invention represented by (c) to (e) above, a ring is formed by a disulfide bond between cysteine residues.

When forming a ring using a spacer in the peptide of the present invention, spacers which can be used for a crosslink between amino acid residues of the peptide can be used without restriction. Examples thereof include, but not limited to, for example, alkylene chains having 1 to 12 carbon atoms and alkylene chains having 1 to 30 carbon atoms containing one or more —O—, —NH— or —S— bonds, in addition to those mentioned above.

The BBB permeable peptides of the present invention also include any pharmacologically acceptable salts thereof. Examples thereof include, but not limited to, inorganic acid salts such as hydrochlorides, phosphates, sulfates and the like, organic acid salts such as acetates, trifluoroacetates, malates, succinates, tartrates, lactates, citrates, maleates, fumarates, sorbates, ascorbates, salicylates, phthalates, methanesulfonates, trifluoromethylsulfonates, benzenesulfonates and the like, inorganic salts such as ammonium salts and the like, alkali metal salts such as sodium salts, potassium salts and the like, alkaline earth metal salts such as calcium salts, magnesium salts and the like, salts of acidic groups such as carboxylates, salts with organic bases such as lower alkylamines such as methylamine, ethylamine, cyclohexylamine and the like and substituted lower alkylamines such as diethanolamine, triethanolamine and the like; etc.

The BBB permeable peptides of the present invention also include derivatives thereof. The derivatives refer to ones obtained by altering the functional group of the peptide of the present invention by modification, addition, alternation, substitution, deletion or the like according to known methods. Examples thereof include those obtained by modifying the N-terminal, the C-terminal, or the amino acid side chain of the peptide of the present invention with a protective group or other substituents and the like. Examples of the derivatives include, but are not limited to, those obtained by acetylation, amidation, acrylication, anilidation, aldehydeation, carbamylation, guanidylation, glycosylation, succinylation, sulfonization, dansylation, nitration, palmitoylation, maleylation, biotinylation, benzyloxycarbonylation, formylation, myristilization, phosphorylation, monomethylation, dimethylation, trimethylation, acetoacetylation, trifluoroacetylation, trinitrophenylation, polyethylene glycolation, labeling (with, for example, radioactive nuclei for PET, fluorescent dyes, etc.) and the like. When the terminal is free, acetylation of the N-terminal or amidation of the C-terminal is preferable since they impart resistance to exopeptidase decomposing a polypeptide from the terminal.

The peptides of the present invention can be produced by a known genetic engineering method, a chemical synthesis method, or the like. The peptides of the present invention can be produced according to a chemical synthesis method, for example, a known peptide synthesis method, but the method is not limited to this. Further, by using an unnatural amino acid in addition to a natural amino acid as a material, the BBB permeable peptide of the present invention in which at least a part of the peptide is composed of an unnatural amino acid can be prepared. Examples thereof include peptides, parts of which are composed of D-form or N-methylated amino acids. As a method for synthesizing peptides, for example, solid phase synthesis methods, liquid phase synthesis methods and the like are mentioned, and after the synthesis reaction, the peptides of the present invention can be isolated and purified by using purification methods usually used in peptide synthesis field, for example, technologies such as solvent extraction, distillation, column chromatography, liquid chromatography, recrystallization and the like in combination.

(2) Target Molecule

The BBB permeable peptides of the present invention have BBB permeability, and when used with other molecules (sometimes referred to as "target molecule" in the present specification), helps the BBB permeation of the target molecule and enables the transfer of the target molecule into the brain. Examples of the target molecule include, but not limited to, molecules that are substances having physiological activity in the brain (hereinafter, may be simply referred to as physiologically active substance) or substances exerting a function in the brain (hereinafter, these may be collectively referred to as intracerebral active substance), or molecules capable of containing or retaining the intracerebral active substance and being used for drug delivery (in the present specification, referred to as drug delivering carrier molecule or also simply as carrier molecule). In the latter case, by using the BBB permeable peptide of the present invention, the carrier molecule can penetrate the BBB and is transferred into the brain together with an intracerebral active substance contained or retained therein. In addition, the BBB permeable peptide of the present invention can allow a larger target molecule to permeate (transfer into the brain), as compared with conventional BBB permeable peptides.

The states of both the target molecule and the peptide of the present invention in achieving BBB permeation of the target molecule are not particularly limited. For example, BBB permeation of the target molecule can be done by placing under the condition in which the target molecule presents with the peptide of the present invention. Further, by forming a complex of the target molecule and the peptide of the present invention, the target molecule can permeate the BBB together with the peptide of the present invention. This makes it possible to transfer the target molecule into the brain together with the peptide of the present invention.

The mode of bonding in the complex of the peptide of the present invention and the target molecule is not particularly limited as long as they may be bonded to the extent that delivery of the target molecule into the brain can be achieved, and includes either mode of covalent bond or non-covalent bond. The bonding mode capable of stably maintaining the bonding in blood is preferable. The bonding between the peptide of the present invention and the target molecule (for example, covalent bond or non-covalent bond) can be carried out by a known method, and an appropriate method can be selected according to the type of the peptide of the present invention and the target molecule to be used. For example, the target molecule may be bonded to the peptide of the present invention using bonding modes used for crosslinking amino acids such as a disulfide bond, an amide bond, a thiol bond or an olefin bond and the like, electrostatically bonds, or biotin-avidin interactions.

The peptide of the present invention and the target molecule may be optionally bonded via a spacer. Usable spacers can be appropriately selected depending on bonding mode and the type of the molecule to be bonded. When the peptide of the present invention is bonded to other molecules using a covalent bond, examples thereof include, but not limited to, alkylene chains having 1 to 12 carbon atoms, alkylene chains having 1 to 30 carbon atoms containing one or more —O—, —NH— or —S— bonds, polyethylene glycol and the like.

When the peptide of the present invention is added to a drug delivering carrier molecule, the mode of bonding is not particularly limited, and they may be bonded to the extent that it does not prevent the carrier molecule from retaining the intracerebral active substance and that transfer of the carrier molecule into the brain can be achieved. For example, the bonding mode includes both covalent bond and non-covalent bond, but is preferably the bonding mode capable of stably maintaining the bonding in the blood. The bonding between the peptide of the present invention and the carrier molecule (for example, covalent bond or non-covalent bond) can be carried out by a known method, and an appropriate method can be selected according to the type of the peptide of the present invention and the carrier molecule to be used.

The target molecules (intracerebral active substances and carrier molecules) that can be used with the peptide of the present invention or can form a complex with the peptide of the present invention will be described below, but the target molecules that can be used for the purpose of BBB permeation and/or delivery into the brain, in relation to the peptides of the present invention, is not limited to the followings.

Examples of the physiologically active substance include, but not limited to, small molecular compounds, polypeptides, oligopeptides, proteins and nucleic acids.

The small molecular compound includes, but are not limited to, compounds contained as active ingredients in pharmaceutical products used for treatment and/or prevention of various diseases related to the brain and central nerve system, for example, active ingredients of therapeutic agents for central nervous system diseases, or compounds used for treatment and/or prevention of brain diseases, for example, compounds with antiinflammatory activity to suppress inflammation in the brain, compounds with anticancer activity, compounds that are active ingredients of antibacterial and antiviral drugs for treatment of intracerebral infections, and the like.

A complex composed of these small molecular compounds and the peptide of the present invention can be formed using a known method. For example, the small molecular compound and/or the peptide of the present invention may be chemically modified, and they may be bonded, optionally via a spacer, but the method is not limited to this. A complex composed of a small molecular compound which is the target molecule and the peptide of the present invention is also included in the present invention.

The proteins include, but not limited to, protein molecules having physiological activity in the brain, and includes proteins used for treatment and/or prevention of diseases. Examples thereof include enzymes, antibodies, transcription factors, or specific parts partially constituting them.

A complex composed of these proteins with the peptide of the present invention can be formed using a known method. For example, the protein and/or the peptide of the present invention may be chemically modified, and they may be bonded, optionally via a spacer, but the method is not limited to this. Alternatively, the protein and the peptide of the present invention may be bonded non-covalently, for example, electrostatically. Furthermore, it is also possible to produce a complex as a fusion protein having both the amino acid sequence of the protein as the target molecule and the amino acid sequence of the peptide of the present invention (preferably a fusion protein having the sequence of the peptide of the present invention at the N-terminal or C-terminal), using a genetic engineering technique. It is also possible to insert an arbitrary sequence between the sequence of the protein which is the target molecule and the sequence of the peptide of the present invention. A complex composed of a protein as the target molecule and the peptide of the present invention is also included in the present invention.

Examples of the peptides (polypeptide and oligopeptide) include physiologically active peptides, and include peptides used for treatment and/or prevention of diseases related to the brain and the central nervous system. Specific examples thereof include, but not limited to, somatostatin, which regulates enzyme expression involved in brain amyloid beta peptide degradation, insulin, which controls neuronal function in the brain, or other peptides related to brain and central nervous system function, and their derivatives.

A complex composed of these peptides with the peptide of the present invention can be formed using a known method. Examples thereof include, but not limited to, the following methods. A peptide having a sequence containing both the peptide as the target molecule and the peptide of the present invention (sometimes including an arbitrary amino acid sequence therebetween) can be synthesized by using a technique for peptide synthesis. The peptide as the target molecule and/or the peptide of the present invention may be chemically modified, and they may be bonded, optionally via a spacer. Alternatively, both may be bonded non-covalently. Furthermore, it is possible to produce a complex as a fusion peptide having both the amino acid sequence of the peptide as the target molecule and the amino acid sequence of the peptide of the present invention (preferably a fusion peptide having the sequence of the peptide of the present invention at the N-terminal or C-terminal), using a genetic engineering technique, and additionally, it is also possible to insert an arbitrary sequence between the sequence of the peptide as the target molecule and the sequence of the peptide of the present invention. A complex composed of a peptide as the target molecule and the peptide of the present invention is also included in the present invention.

The nucleic acids include nucleic acids used for treatment and/or prevention of diseases related to the brain and the central nervous system. Examples thereof include, but not limited to, nucleic acids for treatment of various diseases using gene knockdown methods or using RNA interference, for example, antisense nucleic acids (DNA and RNA), hetero double-stranded nucleic acids, siRNA and shRNA. Specific examples thereof include, but not limited to, gene therapy for amyotrophic lateral sclerosis.

A complex composed of these nucleic acids and the peptide of the present invention can be formed using a known method. For example, the nucleic acid and/or the peptide of the present invention may be chemically modified, and both may be bonded, optionally via a spacer, but the method is not limited to this. Alternatively, the nucleic acid and the peptide of the present invention may be bonded non-covalently, for example, electrostatically. A complex composed of a nucleic acid as the target molecule and the peptide of the present invention is also included in the present invention.

Examples of the drugs which can be preferably used as the physiologically active substance include, but not limited to, antiparkinson's disease drugs, anti-dementia drugs and psychotropic drugs. Since the BBB permeable peptide of the present invention promotes permeation of molecules that do not permeate the BBB or have low permeability, a complex containing a molecule that exhibits a more effective medicinal effect based on the promotion of absorption into the brain is within the scope of the present invention.

The substance that exerts a function in the brain is a molecule that exerts a function other than physiological activity in the brain. Examples thereof include molecules used as a marker in the brain and molecules used for imaging the brain or the target in the brain (in the present specification, referred to as an intracerebral imaging molecule). Examples thereof include, but not limited to, compounds that can visualize the target in vivo, such as fluorescent dyes, quantum dots, nanomagnetic materials, nanogolds, intracellular molecule visualization reagents, labeled molecules that can be detected by PET, and the like.

A complex composed of these substances with the peptide of the present invention can be formed using a known method. A complex composed of these substances as the target molecule and the peptide of the present invention is also included in the present invention.

Examples of the carrier molecule include, but not limited to, liposomes, nanocarriers, cyclodextrin, polyrotaxanes, exosomes and derivatives thereof, micelles or microcapsules. The methods for taking up an intracerebral active substance into the carrier molecule are known, and the known methods can also be used in the present invention. Additionally, for each carrier molecule, various examples including production methods and acquisition routes are known and can be used.

By adding the peptide of the present invention to these carrier molecules, the BBB permeability of the carrier molecule can be promoted. For example, the peptide of the present invention can be covalently or non-covalently bonded to a carrier molecule to prepare the carrier molecule to which the peptide of the present invention is added (hereinafter, may be referred to as the intracerebral delivery carrier of the present invention). Then, by combining the intracerebral delivery carrier of the present invention with an intracerebral active substance, which is a molecule to be transferred into the brain, the transfer of the intracerebral active substance into the brain can be achieved. Further, for example, the peptide of the present invention may be covalently or non-covalently bonded to the carrier molecule containing an intracerebral active substance (for example, liposome, nanocarrier, exosome, phage, polyrotaxane). The bonding between the peptide and the carrier molecule (for example, covalent bond or non-covalent bond interaction) can be carried out by a known method, and the method can be appropriately selected depending on the type of the carrier molecule to be used. For example, in the case with the liposome, by adding a fatty acid to the C-terminal of the peptide of the present invention, it can be inserted in the liposome membrane (see, WO2013/140643). The insertion of the peptide into the liposome membrane may be carried out before or after enclosing an intracerebral active substance in the liposome. Further, it is also possible to bond the peptide of the present invention to the surface of a liposome or cyclodextrin that can enclose an intracerebral active substance, resulting that the peptide presents thereon, using a known method. The methods for enclosing an intracerebral active substance in a liposome are variously reported, and these methods can be appropriately varied and then used in the present invention. For example, it is possible to produce liposome nano particles by the thin film hydration method using an active substance and a liposome raw material into which the peptide of the present invention has been inserted (see, e.g., Ind J Clin Biochem 32 (2): 230-234), but the method is not limited to this. These carrier molecules to which the peptide of the present invention has been added, and the carrier molecules containing or retaining an intracerebral active substance, to which the peptide of the present invention has been added, are also included in the present invention.

In addition, a phage can also be used as the carrier molecule, and the peptide of the present invention and the target molecule can coexist by causing the phage to present the target molecule with the peptide of the present invention. For example, the peptide of the present invention and the antibody or the like can coexist on the phage by presenting the antibody or the like on the phage in addition to the peptide of the present invention, but not limited to this.

As described above, the carrier for intracerebral delivery comprising the carrier molecule to which the peptide of the present invention has been added (for example, liposome, nanocarrier, cyclodextrin, polyrotaxane, exosome and derivatives thereof, phage, micelle or microcapsule) is provided, and it is possible to construct a highly versatile BBB permeable drug delivery system (intracerebral delivery DDS) using the carrier for intracerebral delivery.

Hence, the BBB permeable peptide of the present invention and the carrier molecule for drug delivery to which the BBB permeable peptide of the present invention has been added are also carries for intracerebral delivery for delivering a molecule that does not permeate BBB or has low BBB permeability into the brain.

The BBB permeable peptide of the present invention or the complex containing the BBB permeable peptide of the present invention and the target molecule (intracerebral active substance and carrier molecule for drug delivery) can be further combined with a substance selected from the group consisting of transferrin, fibrinogen, and a peptide containing an RGD sequence, to enhance the BBB permeability.

Accordingly, the present invention also provides a composition containing the BBB permeable peptide of the present invention, the target molecule (intracerebral active substance and carrier molecule for drug delivery), and a substance selected from transferrin, fibrinogen, or a peptide containing an RGD sequence. Preferably, it is a composition containing the BBB permeable peptide of the present invention, the target molecule (intracerebral active substance and carrier molecule for drug delivery), and transferrin.

Further, the present invention is also a complex containing the BBB permeable peptide of the present invention, the target molecule (intracerebral active substance and carrier molecule for drug delivery), and a substance selected from transferrin, fibrinogen, or a peptide containing an RGD sequence. Preferably, it is a complex containing the BBB permeable peptide of the present invention, the target molecule (intracerebral active substance and carrier molecule for drug delivery), and transferrin.

Transferrin is a glycoprotein that transports iron ions in the blood. The origin of transferrin that can be used in the present invention is not particularly limited, but it is preferably derived from humans.

Fibrinogen is a coagulation factor produced in the liver and is a precursor of fibrin, which forms the skeleton of blood clots. The origin of fibrinogen that can be used in the present invention is not particularly limited, but it is preferably derived from humans.

The peptide containing the RGD sequence is, for example, a peptide having a sequence containing 100 or less amino acids, preferably having a sequence containing 50 or less amino acids, further preferably having a sequence containing 20 or less amino acids, and more further preferably having a sequence containing 10 or less amino acids, containing the RGD sequence. The RGD motif is a cell adhesion active sequence common to many cell adhesion proteins.

Examples of the complex containing the BBB permeable peptide of the present invention, the carrier molecule for drug delivery and transferrin include, but not limited to, complexes in which transferring and the BBB permeable peptide of the present invention are bonded to the surface of liposomes, nanocarriers, cyclodextrin, polyrotaxanes, exosomes and derivatives thereof, phages, micelles or microcapsules, and it is also an intracerebral delivery carrier for delivering an intracerebral active substance into the brain. Preferably, it is a liposome carrying transferrin and the BBB permeable peptide of the present invention bonded to the surface. The method for bonding transferrin to the surface of a liposome is known, and this can be used in the present invention. Alternatively, the liposome carrying transferrin bonded to the surface is also commercially available. The method for bonding the BBB permeable peptide of the present invention to the surface of a liposome is as described above. The ratio of transferrin to the BBB permeable peptide of the present invention bonded onto a liposome is not particularly restricted, and appropriately adjusted.

Examples of the complex containing the BBB permeable peptide of the present invention, the carrier molecule for drug delivery and a peptide containing the RGD sequence include, but not limited to, complexes in which a peptide containing the RGD sequence and the BBB permeable peptide of the present invention are bonded to the surface of liposomes, nanocarriers, cyclodextrin, polyrotaxanes, exosomes and derivatives thereof, phages, micelles or microcapsules, and it is also an intracerebral delivery carrier for delivering an intracerebral active substance into the brain. Preferably, it is a liposome in which a peptide having the RGD sequence and the BBB permeable peptide of the present invention are bonded to the surface. The method for bonding a peptide containing the RGD sequence to the surface of a liposome is known, and this can be used in the present invention. The method for bonding the BBB permeable peptide of the present invention to the surface of a liposome is as described above. The ratio of a peptide containing the RGD sequence to the BBB permeable peptide of the present invention bonded onto a liposome is not particularly restricted, and appropriately adjusted.

Animals to which the BBB permeable peptide of the present invention can exhibit BBB permeability is not particularly limited as long as it is an animal having BBB, but is preferably a mammal, for example, human, monkey, cow, horse, goat, dog, cat, rabbit, rat, mouse, rabbit and the like. It is preferably human.

The BBB permeable peptide of the present invention containing the sequence shown in SEQ ID NO: 1 contains proline in the 7-amino acid sequence portion, which facilitates a cyclic structure. Hence, it is considered that the BBB permeability is excellent.

Furthermore, the BBB permeable peptide of the present invention enables BBB permeation of a very large molecule called M13 phage. Hence, the BBB permeable peptide of the present invention is excellent for delivering a large target molecule into the brain.

The complex containing the BBB permeable peptide of the present invention and the target molecule (intracerebral active substance or carrier molecule for drug delivery) can be used as a drug. A pharmaceutical product containing the complex of the present invention can be formulated and administered according to a known method. For example, it can be administered parenterally or orally to mammals including humans as a liquid preparation as it is or as a pharmaceutical composition having a suitable dosage form. Examples of the parenteral administration method include injections or patches (transdermal administration). The pharmaceutical composition containing the complex of the present invention is preferably administered parenterally.

The pharmaceutical composition containing the complex of the present invention may appropriately contain any component as long as the effects of the target molecule and the BBB permeable peptide of the present invention are not impaired. Examples of the optional component include, but not limited to, cross-linking agents, solubilizers, emulsifiers, moisturizers, refreshing agents, inorganic powders, antioxidants, preservatives, colorants, flavoring agents, pH adjusters and stabilizers.

The dose of the complex of the present invention to humans is appropriately determined according to the type of the active substance contained, the age, body weight, condition and sex of the administration subject, the administration method, and other conditions. For example, the dose of the active substance may be about 0.01 mg/kg to about 10 mg/kg per day.

EXAMPLES

Hereinafter, the present invention will be specifically described with reference to examples, but the present invention is not limited to the following examples.

(Example 1) Screening of Bbb Permeable Peptide

Figure 2:
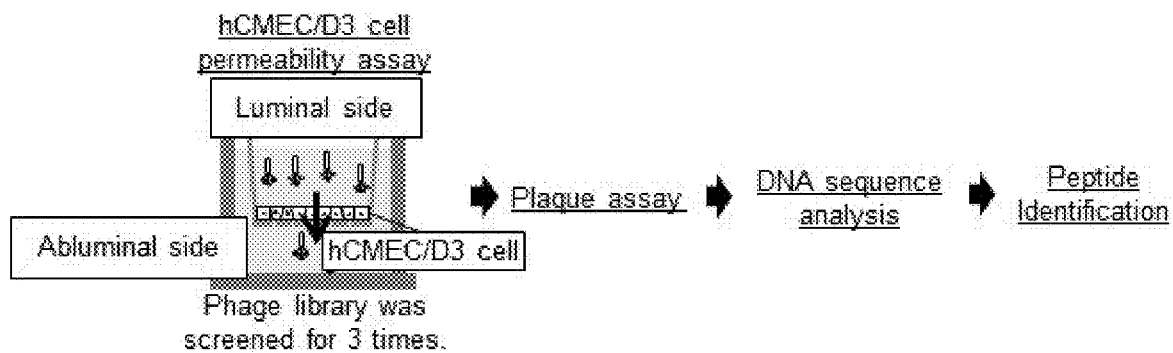
FIG. 2 outlines the process of screening BBB permeable peptides with hCMEC/D3 cells using cyclic amino acids randomly displayed on a phage.
Figure 3:
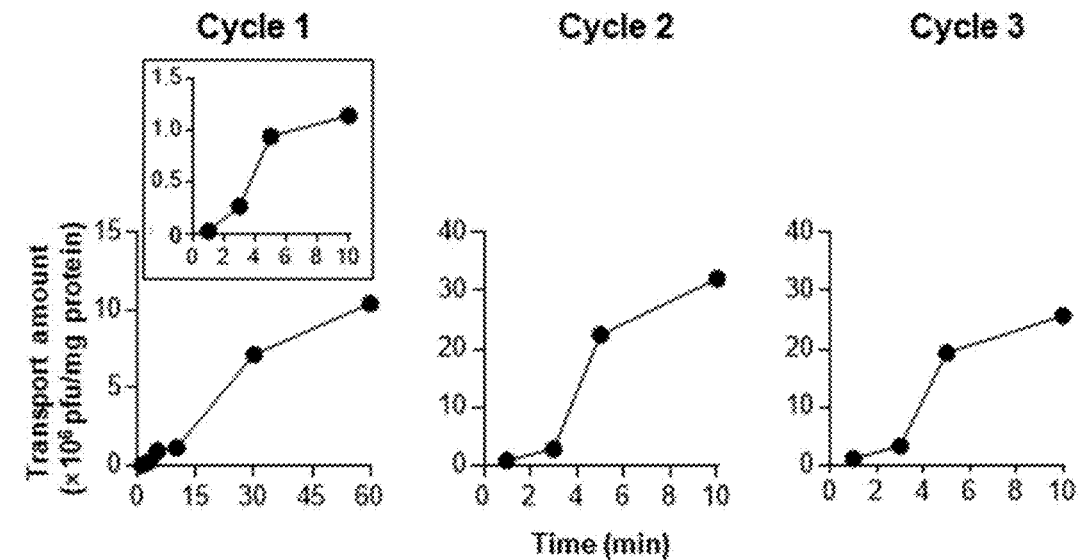
FIG. 3 shows the results of measuring permeation amount of a phage in the first, second and third time-screening for the phage library by using the hCMEC/D3 cell permeation experiment.

Screening of peptides was carried out for the purpose of identification of the peptide which permeates BBB efficiently. For screening of peptides, a phage library ($1 \times 10^9$ types) in which 7 amino acids are randomly presented and hCMEC/D3 cells, which are human BBB model cells, were used.
(1) Production of Phage Library
Ph.D.-C7C Phage Display Peptide Library Kit (New England BioLabs) was purchased, and a phage library was obtained. Cyclic peptides with 7 amino acids sandwiched between cysteines forming a disulfide bond are randomly presented on the phage. The cyclic peptide structure displayed on the phage is shown in FIG. 1.
(2) Screening of Permeable Peptide
A permeability experiment using the hCMEC/D3 cells was performed as follows. The outline is shown in FIG. 2. The hCMEC/D3 cells were seeded on Transwell at $1.0 \times 10^5$ cells/well, and cultured in a $CO_2$ incubator at 37° C. for 4 to 6 days. The phage library ($1.0 \times 10^{11}$ pfu) was added to the luminal side of the cells, and the titer of the phage permeated to the abluminal side was measured by a plaque count method. The phage permeated to the abluminal side was collected, and proliferated using ER2738, and used in the second screening. Screening of the phage library by the hCMEC/D3 cell permeation experiment was repeated three times. The results of permeation of the phage to the abluminal side at respective times are shown in FIG. 3. Sequence analysis of phage DNA was conducted using the plaque of the phage permeated to the abluminal side at the third time, to determine the amino acid sequence of the cyclic peptide permeating the hCMEC/D3 cells.

As a result, 178 clones were identified from the phage group permeated to the abluminal side at the third time (89 clones from the phage group permeated the hCMEC/D3 cells until 1 minute, 89 clones from the phage group permeated the hCMEC/D3 cells until 3 to 5 minutes). Of these, two clones showing the same sequence were identified. When the permeability of the hCMEC/D3 cells was confirmed for these peptides, it was confirmed that the phage presenting the cyclic peptide having an amino acid sequence: SLSHSPQ (SEQ ID NO: 1) showed remarkable permeability, thus, the phage presenting the peptide (hereinafter, referred to also as SLS-phage) was used in the following experiment.

(Example 2) Permeation Amount in In Vitro BBB Model

Figure 4:
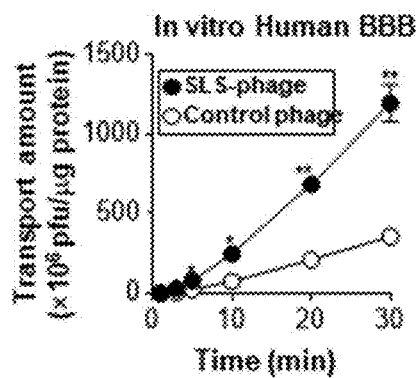
FIG. 4 shows the result of measuring permeation amount of a phage presenting a BBB permeable peptide using an in vitro human BBB model. The data is the mean #SEM (n=3). * $p<0.05$, ** $p<0.01$.

Using an in vitro BBB model, the time-dependent permeation amount of the SLS-phage was measured as described below. The hCMEC/D3 cells were seeded on Transwell at $1.0 \times 10^5$ cells/well, and cultured in a $CO_2$ incubator at 37° C. for 4 to 6 days. The phage ($1.0 \times 10^{11}$ pfu) was added to the luminal side of the cells, and the titer of the phage permeated to the abluminal side was measured by a quantitative PCR method. As a control, a no-peptide presenting phage was used. The results are shown in FIG. 4. The phage (SLS-phage) presenting the cyclic peptide SLSHSPQ (SEQ ID NO: 1) permeated the hCMEC/D3 cells from 1 minute later, and the permeation amount up to 30 minutes was 3.5-fold higher than that of the no-peptide presenting phage.

Figure 5:
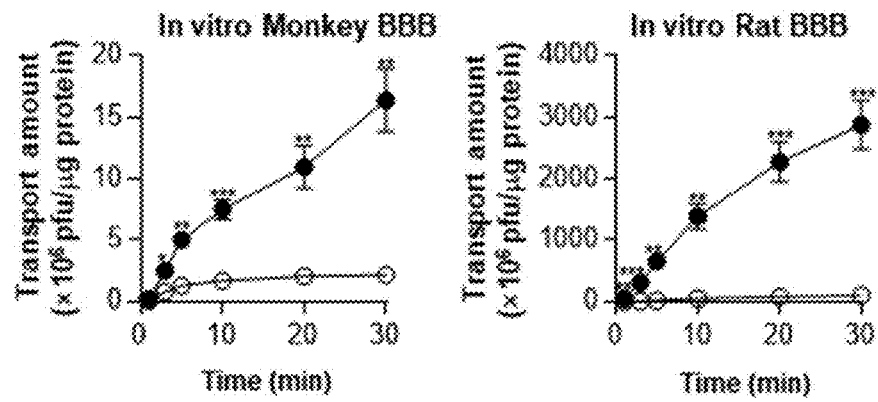
FIG. 5 shows the result of measuring permeation amount of a phage presenting a BBB permeable peptide using an in vitro monkey BBB model or a rat BBB model. The data is the mean±SEM (n=3). * $p<0.05$, ** $p<0.01$, * $p<0.001$.

In addition, the permeation amount was measured using monkey and rat in vitro BBB permeation models. The monkey and rat in vitro BBB kits were purchased from PharmaCo-Cell Company Ltd., and the permeation experiment was conducted in the same manner as for the hCMEC/D3 cells. The results are shown in FIG. 5. The SLS-phage permeated in vitro monkey-derived BBB and rat-derived BBB co-cultured with astrocytes and pericytes at 7.6-fold and 28-fold, respectively.

From this, it was shown that the BBB permeable peptide of the present invention transcellularly permeates cerebral capillary endothelial cells beyond the species.

(Example 3) Uptake of BBB Permeable Peptide of the Present Invention into Cells

The uptake of the BBB permeable peptide of the present invention into the hCMEC/D3 cells was confirmed as follows.

A FAM-labeled synthetic cyclic peptide having the SLSHSPQ (SEQ ID NO: 1) sequence was prepared by requesting Scrum Co., Ltd. A peptide having the sequence of ACSLSHSPQCGGGS (SEQ ID NO: 5), which contains CSLSHSPQC (SEQ ID NO: 6), was chemically synthesized, and then a cyclic peptide was formed by forming a disulfide bond between the cysteine residues. Then, a lysine residue was added to the C-terminal and FAM was further bonded to prepare a FAM-labeled cyclic peptide.

Figure 6:
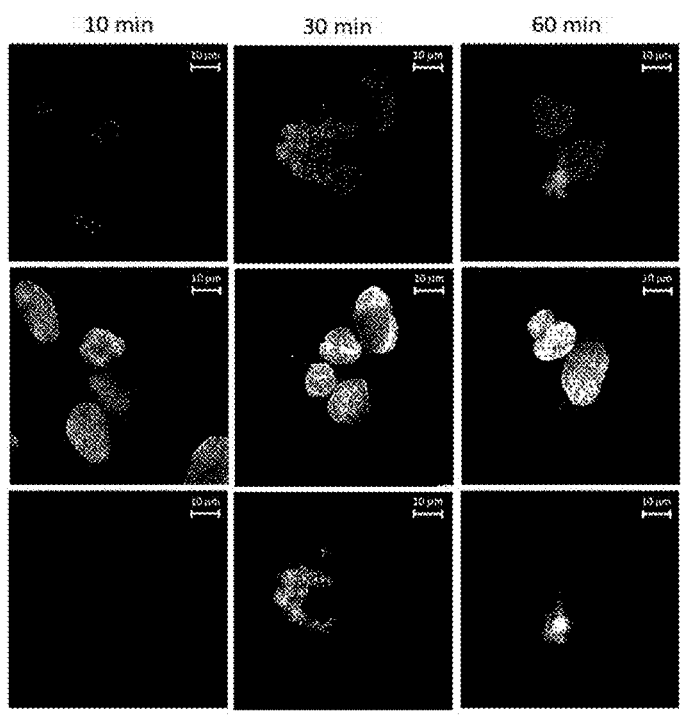
FIG. 6 shows the results of testing uptake of the FAM-labeled peptide SLSHSPQ (SEQ ID NO: 1) of the present invention into hCMEC/D3 cells. The presence of a phage can be confirmed by FAM labeling (green), and the presence of a nucleus can be confirmed by DAPI (blue). Each column shows the results at different observation points, and the upper row is a superposed view in black and white, the middle row is a blue-colored view in black and white and the lower row is a green-colored view in black and white. The bar indicates 10 μm.

The hCMEC/D3 cells were seeded on an 8-well slide glass at $2.5 \times 10^4$ cells/well, and cultured in a $CO_2$ incubator at 37° C. for 48 hours. The FAM-labeled synthetic cyclic peptide SLSHSPQ (SEQ ID NO: 1) (10 UM) was added to the cells, and incubated on a 37° C. hot plate for 10, 30 and 60 minutes. These were washed with 500 μL of cold PBS three times, and fixed with 4% PFA for 10 minutes. VECTASHIELD (registered trademark) Mounting Medium with DAPI was dropped, then, a cover glass was place thereon to enclose it, and FAM and DAPI were observed by a confocal microscopy. The results are shown in FIG. 6. It was confirmed that the FAM-labeled peptide was taken up into the cells. From this, it was confirmed that the synthetic cyclic peptide SLSHSPQ (SEQ ID NO: 1) is internalized in the cell.

Figure 7:
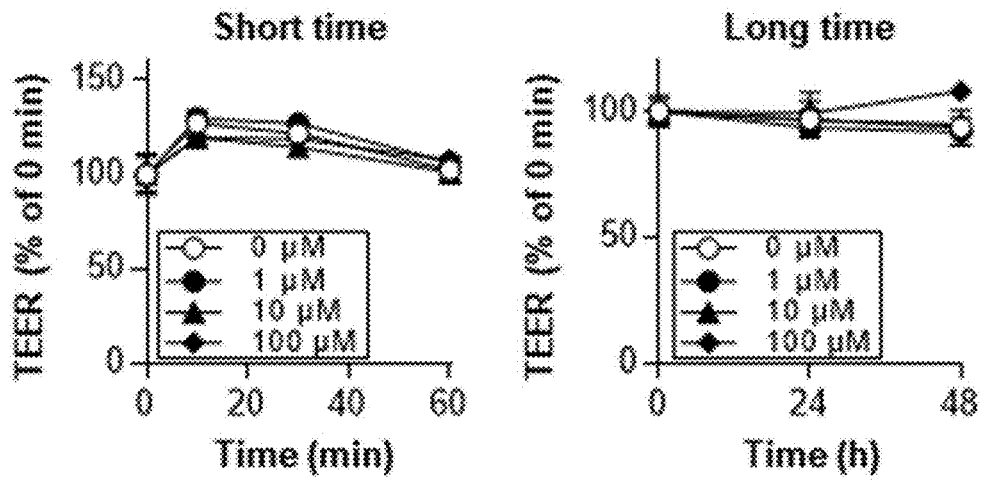
FIG. 7 shows the results of testing the effect of the peptide SLSHSPQ (SEQ ID NO: 1) of the present invention on the tight junction of hCMEC/D3 cells. The data is the mean±SEM (n=3).

(Example 4) Influence of BBB Permeable Peptide of the Present Invention on Tight Junction The influence of the BBB permeable peptide of the present invention having the SLSHSPQ (SEQ ID NO: 1) sequence on tight junction was investigated as described below. The hCMEC/D3 cells was seeded on Transwell at $1.0 \times 10^5$ cells/well, and cultured in a $CO_2$ incubator at 37° C. for 4 to 6 days. The synthetic cyclic peptide SLSHSPQ (SEQ ID NO: 1) (0 to 100 μM) before labeling prepared in Example 3 was added to the cells, and they were incubated in a $CO_2$ incubator at 37° C. The influence on tight junction was evaluated by measuring TEER over time until 48 hours later. As shown in FIG. 7, the cyclic peptide SLSHSPQ (SEQ ID NO: 1) did not reduce the tight junction of the cells.

(Example 5) Cytotoxicity of BBB Permeable Peptide of the Present Invention

Figure 8:
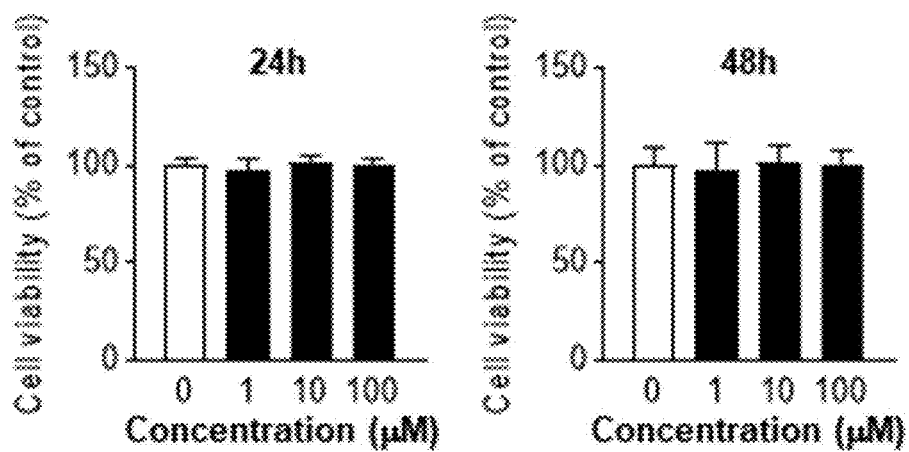
FIG. 8 shows the results of testing the cytotoxicity of the peptide SLSHSPQ (SEQ ID NO: 1) of the present invention.

The influence of the BBB permeable peptide of the present invention having the SLSHSPQ (SEQ ID NO: 1) sequence on cell proliferation was investigated as described below. The hCMEC/D3 cells were seeded on a 96 well plate at $1 \times 10^4$ cells/well, and cultured in a $CO_2$ incubator at 37° C. for 48 hours. The synthetic cyclic peptide SLSHSPQ (SEQ ID NO: 1) (0 to 100 μM) was added to the cells, and incubated in a $CO_2$ incubator at 37° C. The cell viability after 24 and 48 hours was calculated using the cell counting kit-8. As shown in FIG. 8, the synthetic cyclic peptide SLSHSPQ (SEQ ID NO: 1) showed no cytotoxicity to the cells.

Figure 9:
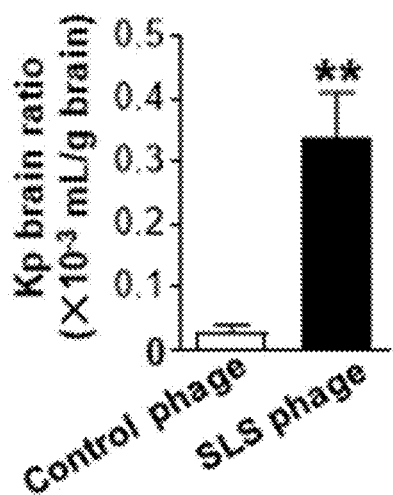
FIG. 9 shows the results of measuring amount of the peptide SLSHSPQ (SEQ ID NO: 1) of the present invention transferred into the brain in mice. The data is the mean #SEM (n=5 to 6). ** p<0.01.

(Example 6) Transfer of BBB Permeable Peptide of the Present Invention into Brain The transfer of the BBB permeable peptide of the present invention having the SLSHSPQ (SEQ ID NO: 1) sequence into the brain was investigated as described below. The SLS-phage and the control phage presenting no peptide (each $1.0 \times 10^{11}$ pfu) were administered intravenously to ICR mice (male, 7 to 10 weeks old), and blood was collected after 1 hour and then PBS perfusion was conducted. The blood was centrifuged at 4° C. and 8000 rpm for 5 minutes to separate plasma. The excised brain was homogenized with a beaded homogenizer at 4000 rpm for 30 seconds×4 times, and subjected to centrifugation at 4° C. and 20000 g for 30 minutes. Then, the supernatant was collected. The titers of the plasma and the brain homogenate supernatant were calculated by the plaque count method. The results are shown in FIG. 9. The brain/plasma ratio of the SLS-phage 1 hour after intravenous administration to mice in vivo was 12-fold higher than that of the control phage.

From the above results, it was shown that the BBB permeable peptide of the present invention exhibits BBB permeability by transcellularly permeating brain capillary endothelial cells.

(Example 7) Confirmation of Transfer to Cerebral Cortex

Figure 10:
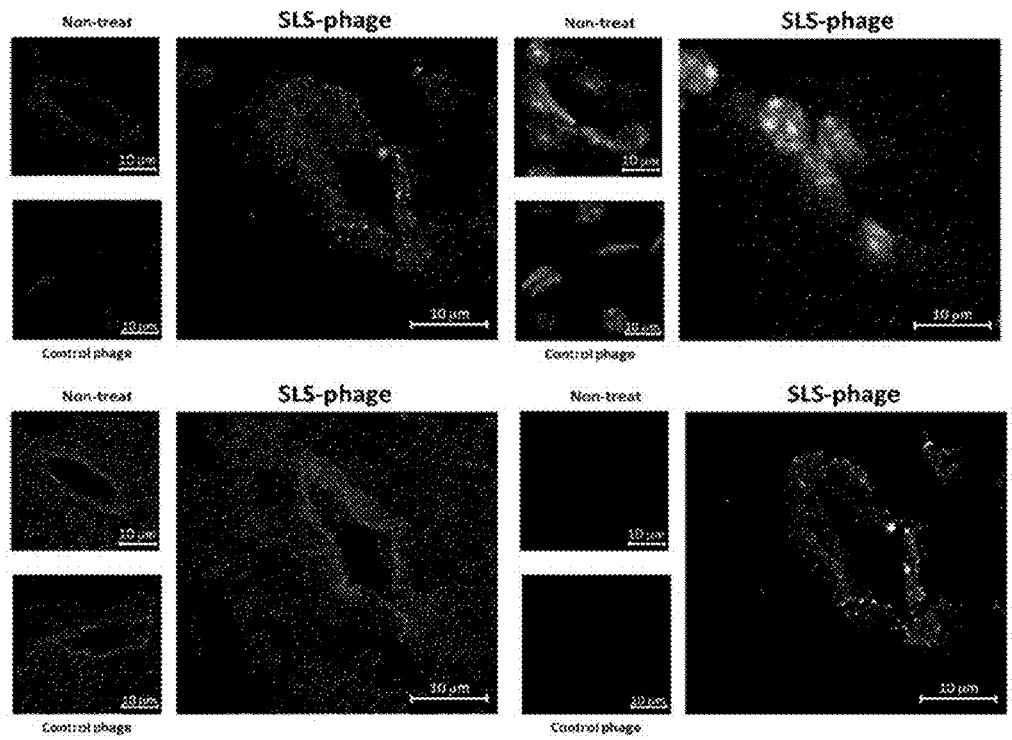
FIG. 10 shows the results of testing the intracerebral transfer of a phage presenting the peptide SLSHSPQ (SEQ ID NO: 1) of the present invention in mice by immunostaining. The presence of a phage can be confirmed by FITC (green), the presence of a blood vessel by lectin (red), and the presence of a nucleus by DAPI (blue). The upper left figure is a superposed view in black and white, the upper right figure is a blue colored view in black and white, the lower left figure is a red colored view in black and white, and the lower right figure is a green colored view in black and white. The bar indicates 10 μm.

The phage was intravenously administered to mice in the same manner as in Example 6, and the excised brain was sectioned. The mouse brain section was immunostained and the presence of the SLS-phage was confirmed. The transfer of the SLS-phage to brain parenchyma was confirmed. The results are shown in FIG. 10.

(Example 8) Inhibition of BBB Permeation by Various Ligands

Using the hCMEC/D3 cells, influences by various ligands (vitronectin, fibrinogen, RGD peptide, transferrin) on the BBB permeability of the phage presenting the peptide SLSHSPQ (SEQ ID NO: 1) of the present invention were tested.

Figure 11:
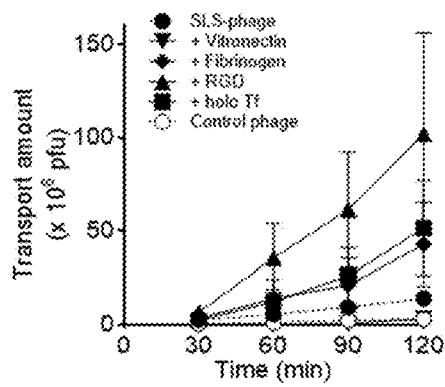
FIG. 11 shows the results of testing the effects of various ligands (vitronectin, fibrinogen, RGD peptide, transferrin) on the BBB permeability of a phage presenting the peptide SLSHSPQ (SEQ ID NO: 1) of the present invention using hCMEC/D3 cells. The data is the mean±SEM (n=3).

The hCMEC/D3 cells were seeded on Transwell at $1.0 \times 10^5$ cells/well, and cultured in a $CO_2$ incubator at 37° C. for 4 to 6 days. The phage ($1.0 \times 10^{11}$ pfu) presenting the peptide SLSHSPQ (SEQ ID NO: 1) was added to the luminal side of the cells, and the titer of the phage permeated to the abluminal side was measured by a quantitative PCR method. As a control, a no-peptide presenting phage was used. In the +vitronectin group, human vitronectin (R&D Systems, Inc.) was added to give 20 μg/mL. In the +fibrinogen group, human fibrinogen (Wako) was added to give 50 μg/mL. In the +RGD group, an RGD peptide (SIGMA) was added to give 100 μM. In the +holo-Tf (transferrin) group, holo-Tf (SIGMA) was added to give 100 μM. Thereafter, the titer of the phage permeated to the abluminal side was measured by quantitative PCR. The results are shown in FIG. 11.

The permeation of the SLS-phage was inhibited by vitronectin. On the other hand, fibrinogen and RGD did not inhibit the permeation of the SLS-phage. Hence, it was suggested that the SLS-phage may permeate via integrin, which is not recognized by fibrinogen or RGD, expressed on the hCMEC/D3 cell.

The permeation of the SLS-phage was promoted by holo-transferrin. Transferrin has an action of promoting secretion of an exosome. Further, it is reported that integrin is transported from cells to cells via exosome secretion. Hence, the SLS-phage may permeate by being secreted from the hCMEC/D3 cell as an exosome. Holo-transferrin may promote exosome synthesis in the polytope by bonding to integrin subtypes to which SLSHSPQ (SEQ ID NO: 1) does not bond, resulting in increased extracellular secretion of the SLS-phage and increased permeation.

(Example 9) Investigation of Cell Permeation Mechanism

Figure 12:
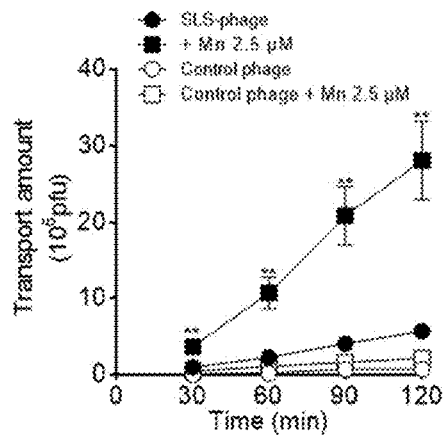
FIG. 12 shows the result of testing the effect of monensin on the BBB permeability of a phage presenting the peptide SLSHSPQ (SEQ ID NO: 1) of the present invention using hCMEC/D3 cells. The data is the mean±SEM (n=3). * p<0.05, ** p<0.01.

The hCMEC/D3 cells were seeded on Transwell at $1.0 \times 10^5$ cells/well, and cultured in a $CO_2$ incubator at 37° C. for 4 to 6 days. The medium at the luminal side and the abluminal side was replaced by a monensin-containing medium, and culture was further performed for 18 hours. The phage ($1.0 \times 10^{11}$ pfu) presenting the peptide SLSHSPQ (SEQ ID NO: 1) was added to the luminal side of the cells, and the titer of the phage permeated to the abluminal side was measured by a quantitative PCR method. The results are shown in FIG. 12. The hCMEC/D3 cell permeation amount of the SLS-phage was increased in a monensin concentration-dependent manner. Thus, it was suggested that the SLS-phage is secreted to the abluminal side from the hCMEC/D3 cell via an exosome.

(Example 10) Intracellular Uptake of Large Molecule Bonded to BBB Permeable Peptide Using the hCMEC/D3 cells, the intracellular uptake of the phage presenting the peptide SLSHSPQ (SEQ ID NO: 1) (SLS-phage) of the present invention was tested.

Figure 13:
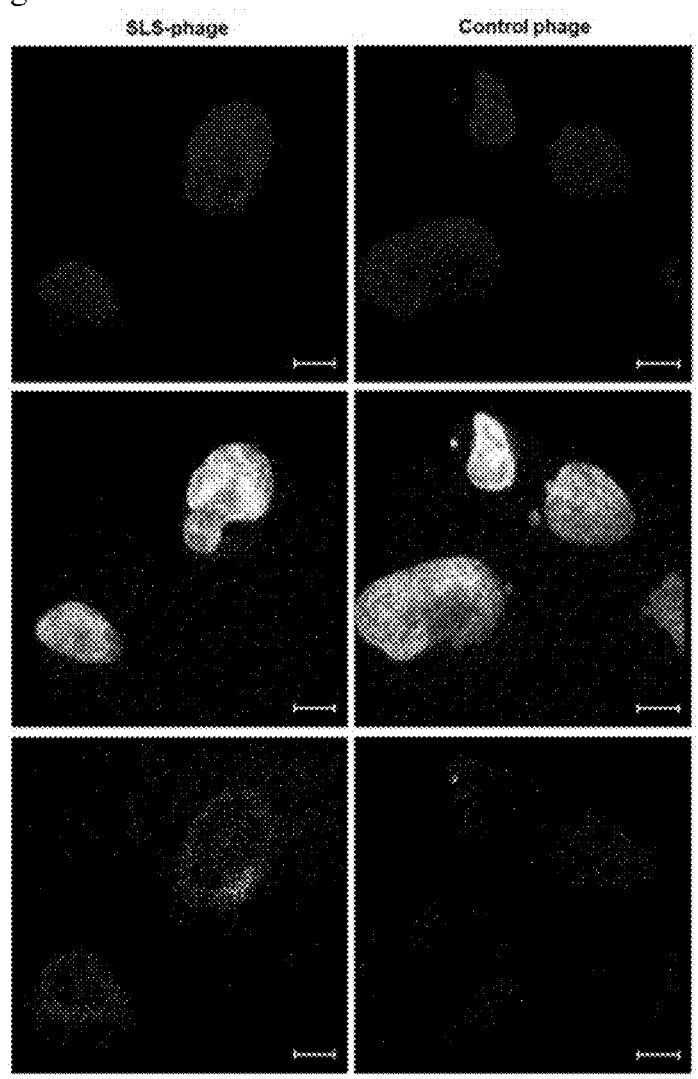
FIG. 13 shows the results of testing the uptake of the SLS-phage of the present invention into hCMEC/D3 cells. The presence of a phage can be confirmed with red and the presence of a nucleus can be confirmed by DAPI (blue). The upper row is a superposed view in black and white, the middle row is a blue-colored view in black and white, and the lower row is a red-colored view in black and white. The bar indicates 10 μm.

The hCMEC/D3 cells were seeded on an 8-well slide glass at $2.5\times10^4$ cells/well, and cultured in a $CO_2$ incubator at 37° C. for 48 hours. The SLS-phage ($1.0\times10^4$ pfu) was added to the cultured cells, followed by incubation on a 37° C. hot plate for 10 minutes. These were washed with 500 μL of cold PBS three times, followed by fixing with 4% PFA for 10 minutes. Thereafter, these were treated with 100 μL of 0.1% triton-X100/PBS for 10 minutes, and 250 μL of 1% BSA/PBS was added, followed by blocking for 1 hour at room temperature. Then, 100 μL of 1% Anti-m13+fd bacteriophage coat proteins antibody/Can Get Signal immunostain B was added, and followed by incubation for 24 hours at 4° C. These were washed with 500 μL of PBS-T three times, and 100 μL of 0.1% Goat Anti-Rabbit IgG H and L (Alexa Fluor 568) (abcam, ab175695)/Can Get Signal immunostain B was added, followed by incubation for 1 hour at room temperature. Again, these were washed with 500 μL of PBS-T three times, and VECTASHIELD (registered trademark) Mounting Medium with DAPI was dropped, then, a cover glass was placed thereon to enclose it, and the SLS-phage and DAPI were observed by a confocal microscope. The results are shown in FIG. 13. It was confirmed that the SLS-phage was taken up into the cells. From these results, it was confirmed that the M13 phage (SLS-phage), which is a very large molecule having the peptide of the present invention, is internalized in the cell.

Next, the mechanism of the intracellular internalization of the SLS-phage was investigated. The SLS-phage was added to the cells cultured in the same manner as described above, and the cells were cultured under conditions changed as follows, and their uptake into the cells was tested. The influence by temperature was tested by culturing at 37° C. or 4° C.

Figure 14:
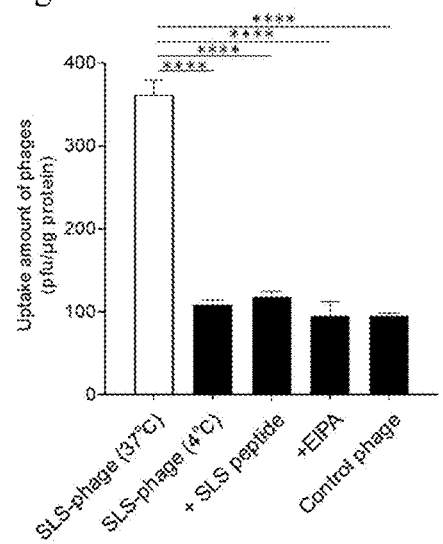
FIG. 14 shows the results of testing the effects of temperature (4° C.), SLS peptide, and ethyl-isopropyl amiloride (EIPA) on the intracellular uptake of SLS-phage.

Furthermore, the SLS-phage was added, and further, the SLS peptide (10 μM) or EIPA (100 μM, purchased from CYAMAN) as a micropinocytosis inhibitor was added, and these were cultured at 37° C., and tested. The results of inhibition of the uptake of the SLS-phage are shown in FIG. 14. It was found that micropinocytosis was involved in the intracellular internalization of the SLS-phage.

(Example 11) Permeation of SLS-Liposome on In Vitro BBB Model

By a thin film hydration method, a fluorescently labeled liposome having the composition: COATSOME NC-50/Cholesterol/DIO (210 nmol/90 nmol/5 nmol) was synthesized, and then the stearylated SLS peptide (ACSLSHSPQ (SEQ ID NO: 7)-stearic acid, purchased from Scrum Co., Ltd.) was mixed to prepare a liposome bonded with the SLS-peptide.

Figure 15:
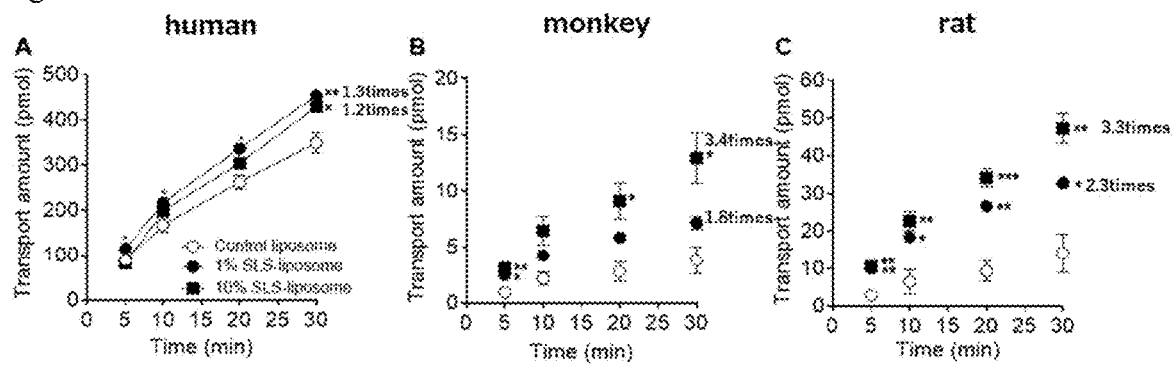
FIG. 15 shows the results of measuring BBB permeability of the SLS-liposome of the present invention using an in vitro BBB model. 15A is a human model, 15B is a monkey model, and 15C is a rat model. The mean±SEM is shown. * p<0.05,  p<0.01, * p<0.001.

The hCMEC/D3 cells were seeded on Transwell at $1.0\times10^5$ cells/well, and cultured in a $CO_2$ incubator at 37° C. for 4 to 6 days. The SLS-liposome (50 nmol) was added to the luminal side of the cells, and the amount of the SLS-liposome permeated to the abluminal side was measured by a fluorescent plate reader. As a control, a liposome without the SLS peptide was used. The results are shown in FIG. 15A. In the liposome bonded with the SLS peptide, permeation was significantly promoted as compared with the control. Permeation was also observed in the control, probably because the degree of tight junction of cells was low and permeation occurred through the gap.

Furthermore, using monkey and rat type in vitro BBB permeability models, the permeation amount of the SLS-liposome was measured. The monkey and rat in vitro BBB kits were purchased from PharmaCo-Cell Company Ltd., and the permeation experiment was carried out in the same manner as for the hCMEC/D3 cell. The results are shown in FIG. 15B and FIG. 15C. The permeation of the SLS-liposome was significantly promoted also in in vitro monkey-derived BBB and rat-derived BBB co-cultured with astrocytes and pericytes.

(Example 12) Intracellular Uptake of SLS-Liposome

Using the hCMEC/D3 cells, the intracellular uptake of the fluorescently labeled SLS-liposome prepared in Example 11 was tested.

Figure 16:
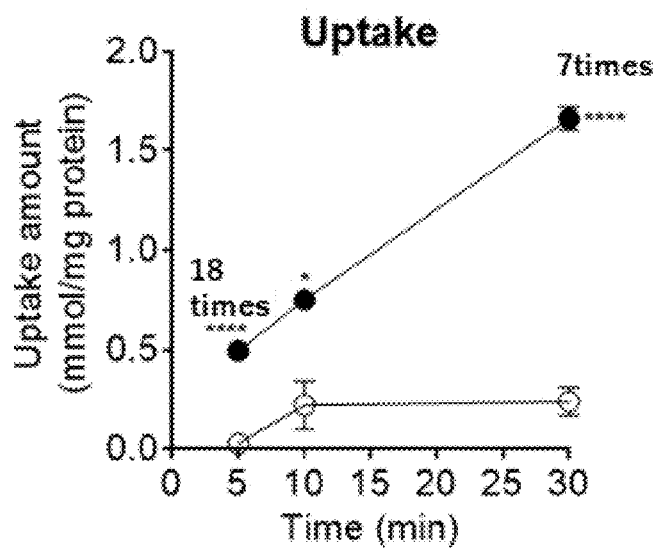
FIG. 16 shows the results of testing uptake of the SLS-liposome of the present invention into hCMEC/D3 cells. *** p<0.001.

The hCMEC/D3 cells were seeded on a 24-well plate at $5.0\times10^4$ cells/well, and cultured in a $CO_2$ incubator at 37° C. for 48 hours. The SLS-liposome or a liposome without SLS as a control was added to the cultured cells (addition amount: 30 nmol), followed by incubation on a 37° C. hot plate for 5, 10 and 30 minutes. Thereafter, the liposome taken up into the hCMEC/D3 cell was extracted with 1% triton-X100/PBS, and measured by a fluorescent plate reader. The results are shown in FIG. 16. It was found that, by bonding the SLS peptide to a liposome, the uptake of the liposome into the cells constituting BBB is significantly promoted.

(Example 13) Transfer of SLS-Liposome into Brain

Figure 17:
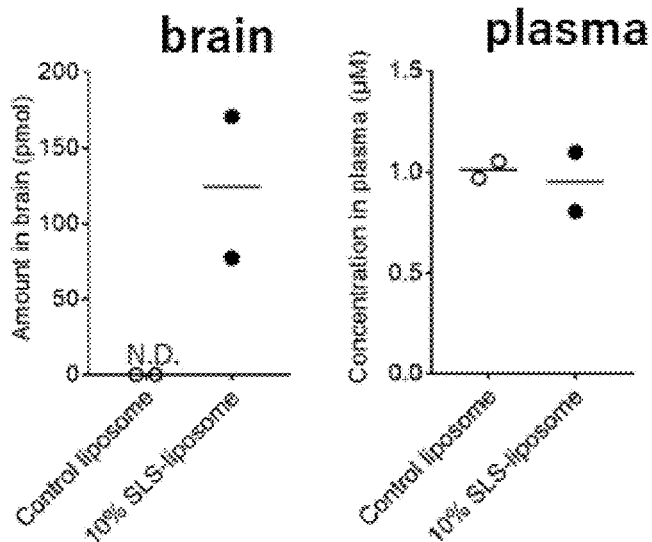
FIG. 17 shows the results of measuring the amount of the SLS-liposome of the present invention transferred into the brain in mice. The results of two cases are shown for each.

The transfer of the SLS-liposome into the brain was investigated as described below. The SLS-liposome prepared in Example 11 and a liposome without SLS (each 50 nmol) were administered intravenously to ICR mice (male, 7 to 10 weeks old), and blood was collected after 55 minutes and PBS perfusion was conducted after 60 minutes, and then the brain was excised. The blood was centrifuged at 4° C. and 8000 rpm for 5 minutes to separate plasma. The excised brain was homogenized with a beaded homogenizer at 4000 rpm for 30 seconds×4 times, followed by centrifugation at 4° C. and 20000 g for 30 minutes, and then the supernatant was collected. The fluorescence amount in the plasma and the brain homogenate supernatant was measured. The results are shown in FIG. 17. The SLS liposome was detected from the brain, but the control liposome was not detected from the brain. The concentration of the SLS-liposome and the concentration of the control liposome in plasma were approximately the same. This indicates that the SLS peptide promotes the transfer of nanocarriers such as a liposome and the like into the brain.

The foregoing merely illustrates objects and subjects of the present invention, and is not intended to be limiting the accompanying Claims. Without departing from the accompanying Claims, various modifications and alterations to the described embodiments will be apparent to those skilled in the art in view of the teachings herein.

INDUSTRIAL APPLICABILITY

The BBB permeable peptide of the present invention can be applied to high-molecular pharmaceutical products and is useful as a permeable peptide. The BBB permeable peptide of the present invention can be further applied to the transfer not only of low-molecular pharmaceutical products but also of high-molecular pharmaceutical products and liposomes into the brain, and is useful as a carrier molecule for the prevention or treatment of diseases related to the brain and central nerve system.

The invention claimed is:

1. A peptide capable of permeating blood-brain barrier comprising at least one of the following amino acid sequences;
   (i) an amino acid sequence consisting of SLSHSPQ (SEQ ID NO: 1), or
   (ii) an amino acid sequence shown in SEQ ID NO: 1, in which P is substituted with an amino acid selected from the group consisting of A, I, L, V, M, F, W, Y, S, T, N, Q, H and G,
   wherein the peptide comprises at least one unnatural amino acid.

2. The peptide according to claim 1, wherein the peptide is a cyclic peptide.

3. A peptide capable of permeating blood-brain barrier which peptide is a peptide selected from the group consisting of the following (a) to (g):
   (a) a peptide consisting of an amino acid sequence: SLSHSPQ (SEQ ID NO:1),
   (b) a peptide having 1 to 5 amino acid(s) at the C-terminal and/or the N-terminal of the amino acid sequence of SLSHSPQ (SEQ ID NO:1) respectively,
   (c) a peptide consisting of an amino acid sequence: CSLSHSPQC (SEQ ID NO: 2) in which the cysteine residues in the sequence are disulfide-bonded,
   (d) a peptide having 1 to 10 amino acid(s) at the C-terminal and/or the N-terminal of the amino acid sequence of CSLSHSPQC (SEQ ID NO: 2) respectively, in which cysteine residues in the sequence are disulfide-bonded,
   (e) a peptide represented by an amino acid sequence of the following formula (1) (SEQ ID NO: 3):

$$\text{AAa-C-AAb-SLSHSPQ-AAc-C-AAd}$$
$$\hspace{1.3cm}|\hspace{3.3cm}|$$
$$\hspace{1.3cm}\text{S}\text{———————}\text{S}$$

wherein, AAa and AAd each independently represent 1 to 10 amino acid(s), and AAb and AAc each independently represent 1 to 5 amino acids,
   (f) a peptide having 1 to 15 amino acid(s) at the C-terminal and N-terminal of the amino acid sequence of SLSHSPQ (SEQ ID NO:1) respectively, in which amino acids located on both ends of the peptide are crosslinked together, and
   (g) the peptide as described in any one of (a) to (f) above, in which P in the amino acid sequence SLSHSPQ is substituted with an amino acid selected from the group consisting of A, I, L, V, M, F, W, Y, S, T, N, Q, H and G.

4. The peptide according to claim 3, which comprises at least one unnatural amino acid.

5. A carrier for intracerebral delivery comprising a peptide capable of permeating blood-brain barrier comprising at least one of the following amino acid sequences:
   (i) an amino acid sequence consisting of SLSHSPQ (SEQ ID NO: 1), or
   (ii) an amino acid sequence shown in SEQ ID NO: 1, in which P is substituted with an amino acid selected from the group consisting of A, I, L, V, M, F, W, Y, S, T, N, Q, H and G,
   wherein the carrier for intracerebral delivery further comprises (a) a carrier molecule for drug delivery selected from the group consisting of liposomes, nanocarriers, exosomes, phages, polyrotaxanes, cyclodextrins, microcapsules and micelles, or (b) a substance selected from the group consisting of transferrin and fibrinogen.

6. A complex comprising:
   a peptide capable of permeating blood brain-barrier comprising at least one of the following amino acid sequences:
      an amino acid sequence consisting of SLSHSPQ (SEQ ID NO:1), or
      an amino acid sequence shown in SEQ ID NO:1, in which P is substituted with an amino acid selected from the group consisting of A, I, L, V, M, F, W, Y, S, T, N, Q, H and G; and
   a molecule that permeates the blood-brain barrier with the peptide,
   wherein the molecule is a molecule that exhibits a pharmacological action in the brain or an intracerebral imaging molecule.

7. The complex according to claim 6, further comprising a substance selected from the group consisting of transferrin, fibrinogen, and a peptide containing RGD sequence.

8. The complex according to claim 6, wherein the molecule is a small-molecular compound, a polypeptide, an oligopeptide, a protein or a nucleic acid.

9. A pharmaceutical composition for preventing and/or treating a brain disease comprising:
   a peptide capable of permeating blood-brain barrier comprising at least one of the following amino acid sequences:
   (i) a sequence consisting of SLSHSPQ (SEQ ID NO:1), or
   (ii) an amino acid sequence shown in SEQ ID NO:1, in which P is substituted with an amino acid selected from the group consisting of A, I, L, V, M, F, W, Y, S, T, N, Q, H and G;
   a drug to be delivered into the brain; and
   a pharmacologically acceptable additive.

10. The pharmaceutical composition according to claim 9, wherein the peptide is a cyclic peptide.

11. The pharmaceutical composition according to claim 9, wherein the peptide is a peptide selected from the group consisting of the following (a) to (g):
   (a) a peptide consisting of an amino acid sequence: SLSHSPQ (SEQ ID NO: 1),
   (b) a peptide having 1 to 5 amino acid(s) at the C-terminal and/or the N-terminal of the amino acid sequence of SLSHSPQ (SEQ ID NO:1) respectively,
   (c) a peptide consisting of an amino acid sequence: CSLSHSPQC (SEQ ID NO: 2) in which the cysteine residues in the sequence are disulfide-bonded,
   (d) a peptide having 1 to 10 amino acid(s) at the C-terminal and/or the N-terminal of the amino acid sequence of CSLSHSPQC (SEQ ID NO: 2) respectively, in which the cysteine residues in the sequence are disulfide-bonded,
(e) a peptide represented by an amino acid sequence of the following formula (1) (SEQ ID NO: 3)

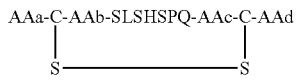

wherein, AAa and AAd each independently represent 1 to 10 amino acid(s), and AAb and AAc each independently represent 1 to 5 amino acids,
(f) a peptide having 1 to 15 amino acid(s) at the C-terminal and N-terminal of the amino acid sequence of SLSHSPQ (SEQ ID NO: 1) respectively, in which amino acids located on both ends of the peptide are crosslinked together, and
(g) the peptide as described in any one of (a) to (f) above, in which P in the amino acid sequence SLSHSPQ (SEQ ID NO: 1) is substituted with an amino acid selected from the group consisting of A, I, L, V, M, F, W, Y, S, T, N, Q, H and G.

12. The pharmaceutical composition according to claim 9, wherein the drug is a molecule that exhibits a pharmacological action in the brain or an intracerebral imaging molecule.

13. The pharmaceutical composition according to claim 12, wherein the molecule that exhibits a pharmacological action in the brain is a small-molecular compound, a polypeptide, an oligopeptide, a protein or a nucleic acid.

14. The pharmaceutical composition according to claim 9, further comprising a substance selected from the group consisting of transferrin, fibrinogen, and a peptide containing RGD sequence.

15. The pharmaceutical composition according to claim 9, further comprising a carrier molecule for drug delivery selected from the group consisting of liposomes, nanocarriers, exosomes, phages, polyrotaxanes, cyclodextrins, microcapsules and micelles.

16. A method for preventing and/or treating a brain disease, comprising administering a prophylactically and/or therapeutically effective amount of a pharmaceutical composition to a subject in need of prevention and/or treatment of the brain disease, the pharmaceutical composition for preventing and/or treating the brain disease comprising:
a peptide capable of permeating blood-brain barrier comprising at least one of the following amino acid sequences:
(i) a sequence consisting of SLSHSPQ (SEQ ID NO:1), or
(ii) an amino acid sequence shown in SEQ ID NO:1, in which P is substituted with an amino acid selected from the group consisting of A, I, L, V, M, F, W, Y, S, T, N, Q, H and G;
a drug to be delivered into the brain; and
a pharmacologically acceptable additive.

* * * * *